US012268888B2

(12) United States Patent
Flakne et al.

(10) Patent No.: US 12,268,888 B2
(45) Date of Patent: Apr. 8, 2025

(54) REMOTE FOLLOW-UP OF NEUROSTIMULATION SYSTEM

(71) Applicant: BIOTRONIK SE & Co. KG, Berlin (DE)

(72) Inventors: Dawn Gayle Flakne, Portland, OR (US); Yarisa Jaroch Gonzalez, West Linn, OR (US); Alan Fryer, Portland, OR (US); Lauren Kraiter, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 245 days.

(21) Appl. No.: 18/172,444

(22) Filed: Feb. 22, 2023

(65) Prior Publication Data

US 2023/0201608 A1    Jun. 29, 2023

Related U.S. Application Data (63) Continuation of application No. 17/260,453, filed as application No. PCT/US2019/044811 on Aug. 2, 2019, now Pat. No. 11,612,753.

(60) Provisional application No. 62/713,587, filed on Aug. 2, 2018.

(51) Int. Cl.
*A61N 1/36*   (2006.01)
*A61N 1/372*  (2006.01)

(52) U.S. Cl.
CPC ..... *A61N 1/37264* (2013.01); *A61N 1/36142* (2013.01); *A61N 1/36146* (2013.01); *A61N 1/37247* (2013.01); *A61N 1/37254* (2017.08); *A61N 1/37282* (2013.01)

(58) Field of Classification Search
CPC ............ A61N 1/37264; A61N 1/36146; A61N 1/37247; A61N 1/37282; A61N 1/37258
See application file for complete search history.

(56) References Cited

U.S. PATENT DOCUMENTS

| | | | |
|---|---|---|---|
| 10,124,177 B2 | 11/2018 | Kumar | |
| 2003/0114899 A1* | 6/2003 | Woods | A61N 1/3787 607/43 |
| 2006/0113396 A1 | 6/2006 | DeRocco et al. | |
| 2006/0195152 A1 | 8/2006 | Gerber | |
| 2011/0118805 A1 | 5/2011 | Wei et al. | |
| 2011/0172737 A1 | 7/2011 | Davis et al. | |

(Continued)

OTHER PUBLICATIONS

International Search Report (PCT/ISA/210) and Written Opinion (PCT/ISA/237) mailed on Oct. 25, 2019, by the U.S. Patent Office as the International Searching Authority for International Application No. PCT/US2019/044811.

*Primary Examiner* — Eugene T Wu
(74) *Attorney, Agent, or Firm* — Buchanan Ingersoll & Rooney PC (57) ABSTRACT

A method for remote programming a therapy device for neurostimulation comprises: generating a stimulation program for the therapy device by means of a clinician programmer; transferring the stimulation program to a patient programmer; loading the stimulation program on the therapy device from the patient programmer; and increasing a stimulation amplitude of the stimulation program by means of the patient programmer. An initial stimulation amplitude setting of the stimulation program is limited to a minimal dose amplitude.

19 Claims, 5 Drawing Sheets

(56) References Cited

U.S. PATENT DOCUMENTS

| | | |
|---|---|---|
| 2014/0350636 A1 | 11/2014 | King et al. |
| 2015/0039047 A1 | 2/2015 | Parker |
| 2016/0045745 A1 | 2/2016 | Mathur et al. |
| 2016/0082267 A1 | 3/2016 | Kothandaraman et al. |
| 2017/0120062 A1 | 5/2017 | Kumar |

* cited by examiner

Clinician Programmer- Edit Mode

Stimulation: ON *(fixed)*
Active program: Program #1 *(fixed)*
Program amplitude: 0 mA *(fixed)*
Max amplitude: 10.0 mA
Electrodes: (+) (-) () ()
Pulse width: 200 us
Frequency: 50 Hz     [Transmit]   [Refresh (lose edits)]

Clinician Programmer- Patient View Mode

Stimulation: ON
Active program: Program #1
Program amplitude: 2.0 mA
Max amplitude: 10.0 mA
Electrodes: (+) (-) () ()
Pulse width: 200 us
Frequency: 50 Hz     [Transmit]   [Refresh]

Fig. 3

Clinician Programmer- Edit Mode + Patient View

Stimulation: ON *(fixed)*
Active program: Program #1 *(fixed)*
Program amplitude: 0 mA *(fixed)*
Max amplitude: 10.0 mA
Electrodes: (+) (-) () ()
Pulse width: 200 us
Frequency: 50 Hz

Transmit

Patient Remote View

Stimulation: ON
Active program:
Program #1
Program amplitude:
2.0 mA

Refresh

REMOTE FOLLOW-UP OF NEUROSTIMULATION SYSTEM

CROSS-REFERENCE TO RELATED APPLICATIONS

This application is continuation application of co-pending U.S. application Ser. No. 17/260,453, filed on Jan. 14, 2021, which is the United States national phase under 35 U.S.C. § 371 of PCT International Patent Application No. PCT/US2019/044811, filed on Aug. 2, 2019, which claims the benefit of U.S. Provisional Patent Application No. 62/713,587, filed on Aug. 2, 2018, the disclosures of which are hereby incorporated by reference herein in their entireties.

TECHNICAL FIELD

The instant invention relates to a method for remote programming a therapy device for neurostimulation as well as to a system for remote programming a therapy device for neurostimulation. In particular, the instant invention relates to methods and systems that facilitate a remote follow-up of a therapy device for spinal cord stimulation (SCS).

BACKGROUND

Generally, an SCS therapy device, such as an implantable pulse generator (IPG) or a trial stimulator, delivers electrical pulses via leads implanted in the epidural space in order to produce a pain-relieving effect. A stimulation program is defined as a set of stimulation parameters, which may include information about the selected electrodes, as well as therapy settings like frequency and/or pattern of pulses, pulse width, and a range of amplitudes, or a combination thereof. These program parameters are usually defined by a user of a clinician programmer (which could be, for example, a clinician or a company representative). The clinician programmer may allow the user to create more than one program option to make available to the patient. Then, the patient can use the patient programmer (sometimes also called patient remote) to select which program is active, and to adjust the amplitude of the program within an allowed range.

In the following, some standard in-office SCS programming functions will be explained. SCS therapy devices are primarily programmed via in-person follow-up sessions. During such a so-called in-office follow-up, the user of the clinician programmer checks the status of the therapy device (e.g., a trial stimulator or an implantable device). The user of the clinician programmer defines program parameters for one or more program options. Usually, as parameters are changed on the clinician programmer, they immediately take effect on the therapy device. The user of the clinician programmer can set all parameters of the therapy device, including amplitude, pulse width, frequency and/or pattern of pulses, and electrode selection, in real-time.

Next, some standard in-home SCS functions will be explained. Existing SCS systems allow the patient to control stimulation via the patient programmer. The SCS system allows the patient to select the active program (from a list of programs that were defined via the clinician programmer) and adjust the stimulation amplitude within the allowed amplitude range. The patient programmer also offers the ability to turn stimulation completely off and back on.

Some commercially available SCS systems offer advanced stimulation control options to the patient via the patient programmer for controlling stimulation, such as frequency, pulse width, or the relative balance of amplitudes between concurrently running stimulation trains (called "areas" or "subprograms") within the program.

A problem that exists with such conventional approaches to SCS programming is that at least some patients require frequent or ongoing adjustment for optimization of the stimulation therapy. The patient programmer used in the home setting has two main limitations in this respect: (1) The technical functionality of conventional patient programmers is limited such that the patient programmer does not have as many programming control options as a clinician programmer; and (2) SCS patients typically do not have the know-how to perform more advanced programming functions via the patient programmer and therefore require a clinical expert to perform the adjustments.

Hence, many presently available systems require that the patient travels to meet with a clinical expert in order to receive reprogramming. For pain patients in particular, traveling can be burdensome and challenging for patients. In some cases, patients choose to skip reprogramming visits and as a result may have non-optimized stimulation therapy.

In order to provide some troubleshooting of stimulation programming without the patient having to come to the clinic, some clinical experts will provide over-the-phone instructions to the patient on changes that can be made via the patient programmer. Some patient programmers have more advanced stimulation parameters available.

U.S. Pat. No. 10,124,177 discloses a system for programming an implanted device when a patient is remote from a clinician. The system includes a patient programmer, a clinician programmer, and a remote diagnostic server configured to facilitate secure communication between the patient programmer and the clinician programmer. The remote diagnostic server is configured to initiate a secure programming session between the patient programmer and the clinician programmer, receive a proposed stimulation program from the clinician programmer, transmit the proposed stimulation program to the patient programmer, receive an indication from the patient programmer that the patient has accepted the proposed stimulation program, and transmit an alert to the clinician programmer, the alert indicating that the patient has accepted the proposed stimulation program.

It is desirable to allow patients to be assisted remotely in order to (1) reduce the need for traveling to in-person follow-up visits, and (2) encourage more frequent and long-term optimization to ultimately achieve better pain relief outcomes.

By assisting patients remotely with programming changes, all advanced programming functionality options can in principle be updated, but since the updates are set up by an expert working remotely, the patient does not need to have the training or expertise to work with advanced programming.

The present disclosure is directed toward overcoming one or more of the above-mentioned problems, though not necessarily limited to embodiments that do.

SUMMARY

It is an object of the present invention to provide an improved method for remote programming a therapy device and a corresponding system. For example, it is desirable to enhance the safety during a remote follow-up procedure, e.g., by avoiding inadvertently causing an uncomfortable or even painful patient experience.

According to a first aspect, a method for remote programming a therapy device for neurostimulation is provided. The method comprises: generating a stimulation program for the therapy device by means of a clinician programmer; transferring the stimulation program to a patient programmer; loading the stimulation program on the therapy device from the patient programmer; and increasing a stimulation amplitude of the stimulation program by means of the patient programmer. In one embodiment, an initial stimulation amplitude setting of the stimulation program is limited, e.g., by the therapy device, to a minimal dose amplitude.

The method may further comprise a step of checking the validity and/or authenticity of the stimulation program, e.g., by means of a secure communications path to the therapy device. This step may be performed before the initial amplitude setting is limited to the minimal dose amplitude.

According to a second aspect, a system for remote programming a therapy device for neurostimulation comprises: a therapy device being configured for providing electrical stimulation pulses for neurostimulation; a clinician programmer being configured for generating a stimulation program for the therapy device; a patient programmer being configured for receiving the stimulation program, the therapy device being configured for receiving the stimulation program from the patient programmer. The clinician programmer may be configured for ensuring that a stimulation amplitude setting of the generated stimulation program is limited to a minimal dose amplitude. Further, the patient programmer may be configured so as to allow for adjusting the stimulation amplitude.

In the following, reference is made to both above-mentioned aspects of the present invention.

For example, the minimal dose amplitude referred to above may correspond to zero amplitude or an amplitude close to zero. For example, the minimal dose amplitude may have a value of 0.1 mV. In particular, the minimal dose amplitude may be such that safety for the patient is guaranteed, i.e., stimulations at the minimal dose amplitude do not cause pain to the patient, for example.

It should be noted that generating said stimulation program may comprise generating an entirely new stimulation program or editing (updating) an existing one. It should also be noted that the therapy device may ensure the amplitude is set to the minimal dose in said stimulation program.

Further, with regard to the system according to the second aspect, it should be noted that the clinician programmer may be configured to automatically ensure that a stimulation amplitude setting of the generated stimulation program is limited to a minimal dose amplitude. In other words, for example, the clinician programmer may be pre-configured such that it places certain restrictions on programming capabilities during a remote follow-up session according to rules that limit the range of parameters available to any program that is edited during remote follow-up, wherein the stimulation amplitude parameter(s) are limited to the minimal dose amplitude according to said rules.

Hence, the present invention ensures that remotely programmed amplitudes are at a low-dose until increased by the patient programmer. By contrast, conventional systems and methods provide that the clinician increases the amplitude by means of the clinician programmer and waits for patient feedback. However, if the remote connection is lost during this procedure, a case may occur, wherein the patient is subject to stimulation at an amplitude that lies outside of an acceptable range and that may potentially cause discomfort or even pain. In that case the clinician would not receive any feedback and would thus not be able to intervene. The present invention avoids such a situation by limiting the initial amplitude to the minimal dose amplitude and thus transferring the control over the subsequent amplitude adjustment to the patient.

For example, in an embodiment, the method may further comprise accepting the transferred stimulation program by means of the patient programmer before it is loaded on the therapy device. Correspondingly, the system may comprise a patient controller in the form of the patient programmer that provides the means for the patient to accept updates. Thus, the patient programmer may be used as a gateway that requires the patient to accept before proceeding with remote programming changes.

In an embodiment, the therapy device is configured for performing a validity check on the newly received stimulation program before loading the stimulation program. For example, the validity check may comprise checking if the stimulation program has an amplitude at minimal dose. Thus, patient safety may be further enhanced by having the patient's therapy device check the authenticity, authorization and validity of the remotely edited programs, including the amplitude being set to minimal dose.

Further, in an embodiment, the clinician programmer may be used to view the stimulation amplitude in near real-time, e.g., to confirm the patient is properly adjusting the amplitude.

In an embodiment, the stimulation program is transferred from the clinician programmer to the patient programmer via a central service unit. Correspondingly, the system may comprise such a central service unit being configured for facilitating communication between the clinician programmer and the patient programmer. For example, this opens up the possibility to use the same clinician programmer interface and/or another interface to a service center to perform the remote programming as is used during in-person follow-ups. The central service unit may also be configured for managing and controlling access rights to therapy devices according to a user's log-in and/or for serving as a central data repository. Such a central service unit may also be referred to as a service center.

In a variant embodiment of the first aspect, before the step of generating the stimulation program, the clinician programmer receives status information of the therapy device. For example, such information may be transferred from the therapy device to the clinician programmer via the patient programmer and a service center, e.g., in the form of a central service unit as described above. For example, the clinician programmer may thus serve as an interface for a clinical expert to view statistical trends, a present status, and/or settings, and/or to make changes to send to the patient's system.

It is also within the scope of the present invention that the patient programmer and/or the therapy device may allow for setting a new stimulation amplitude as a new default amplitude of the stimulation program. For example, the patient may use the patient programmer to increase the stimulation amplitude to an acceptable dose until it reaches an acceptable target amplitude, which may then be saved as the new default amplitude for the stimulation program in the therapy device.

Summarizing, it is proposed to provide for system protections that ensure remotely programmed amplitudes are at a low-dose until increased by the patient programmer. With the instant invention, control over the stimulation amplitude is thus transferred to the patient. After accepting the newly generated or updated stimulation program, the patient may adjust (increase) the amplitude until an acceptable dose is reached. During this follow-up procedure the patient may be in contact (e.g. via telephone) with the clinician who has sent the new stimulation program. The clinician may thus receive immediate feedback regarding the patient's experience and condition. Furthermore, the clinician programmer may be connected with the patient programmer (e.g. via a central service unit) and may thus view the current stimulation amplitude in near real-time. The clinician may thus supervise the adjustment and selection of a suitable stimulation amplitude by the patient.

For example, in accordance with the present invention, remote programming for neurostimulation systems may include the ability to perform the following functions without the patient coming in to the clinic: Checking the status of the patient's system and statistics collected over time (e.g. implanted lead integrity, present stimulation settings, and diagnostic trends related to pain or system use); and tailoring the system to the patient's needs, which may include: changing settings or parameters, making new stimulation options available, changing existing stimulation options, or removing stimulation options. The proposed solution may lead to increased patient satisfaction and better patient outcomes.

All aspects and features of the embodiments described above and in the following can be combined with each other unless explicitly stated otherwise.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein, FIG. 1 schematically and exemplarily illustrates a system for remote programming a therapy device for neurostimulation in accordance with one or more embodiments.

Figure 1:
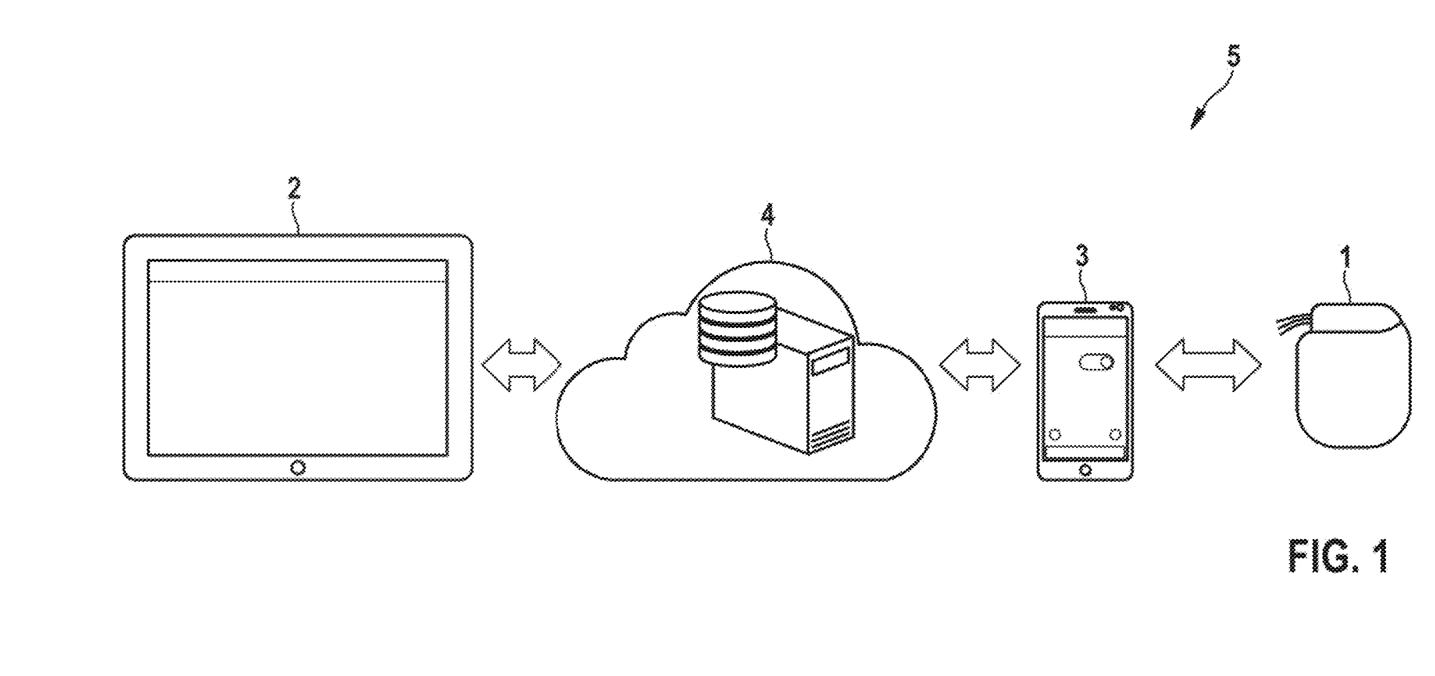

DETAILED DESCRIPTION is FIG. 1 shows schematically and exemplarily components of a system 5 involved in remote follow-up in accordance with one or more embodiments of the present invention. In order to enable remotely checking a system status and providing updates to stimulation programs, the system 5 may comprise several components 1-4. The system components 1-4 and their respective roles will be described in the following.

The system 5 comprises a therapy device 1, which can be, for example, an implantable stimulation device and/or an external stimulation device (such as implantable spinal cord stimulator and/or a spinal cord stimulation trial stimulator). The therapy device 1 may store at least one stimulation program(s), and/or provide therapeutic stimulation via implanted leads and/or a sensing capability.

Further, a programming interface in the form of a clinician programmer 2 is provided. For example, the clinician programmer 2 may be used to remotely query and view a system status, make changes to stimulation parameter settings on the basis of a user's (e.g. clinician expert like physician or company representative) input, and transmit those settings. For example, in an embodiment, the clinician programmer 2 can be the same clinician programmer that is used in-clinic to program the therapy device 1. In other embodiments, the clinician programmer 2 can be a mobile device like a smart phone or a tablet computer, or a desktop computer, which may be equipped with a specific software application (App).

The system 5 further includes a patient programmer 3 that may be used as an interface for the patient to accept remote programming transmissions and control a newly available stimulation program. In an embodiment, the patient programmer 3 can be a mobile device like a smart phone or a tablet computer, which may be equipped with a specific software application (App). In other embodiment, the patient programmer 3 can be a patient device especially made for communication with the therapy device 1.

As a further component, the system 5 may comprise a central service unit 4 that may, for example, fulfill one or more of the following functions:
 a. serve as a central data repository;
 b. manage access rights and control access to therapy device 1, e.g., according to a user's log-in;
 c. facilitate communication to therapy device 1 via the patient programmer 3.

For example, by providing such a central service unit 4, the remote follow-up service is not restricted to the use of a single clinician programmer 2.

In one embodiment, the central service unit 4 can be a cloud-based service center. In another embodiment, the central service unit 4 can comprise a server, server farm, or similar.

Figure 2:
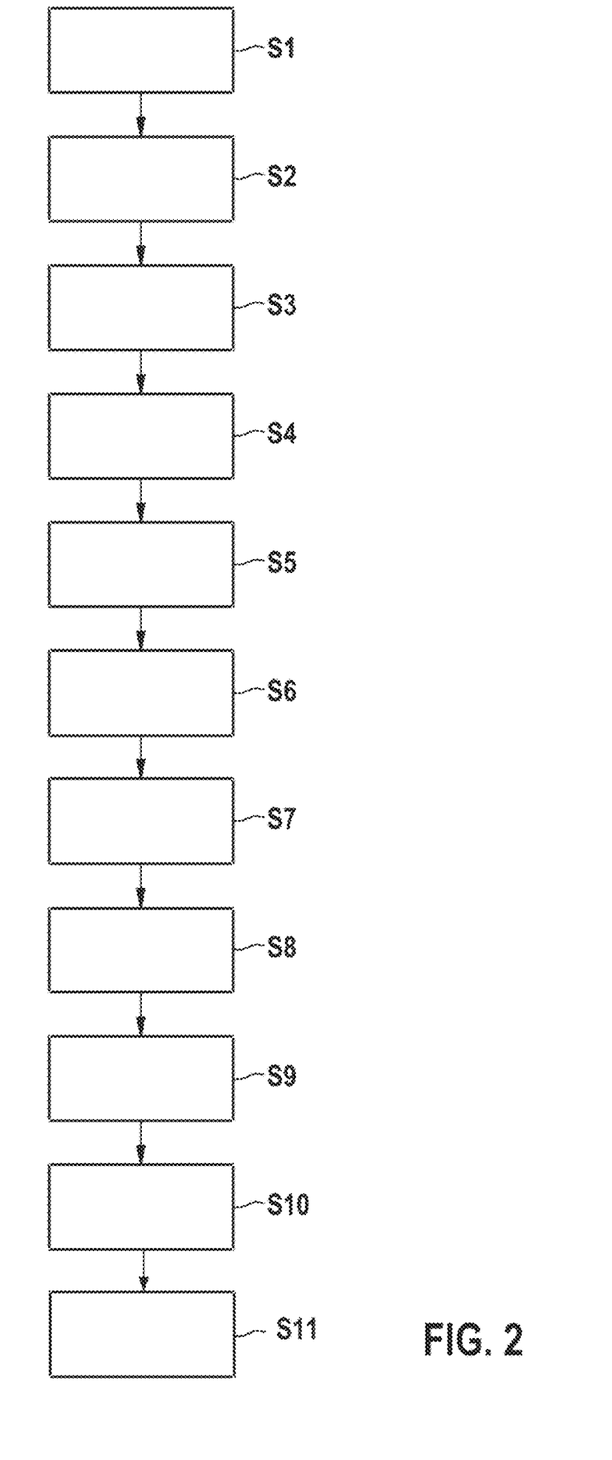
FIG. 2 schematically and exemplarily illustrates steps of a method for remote programming a therapy device for neurostimulation in accordance with one or more embodiments.

FIG. 2 shows an exemplary overview of steps for executing remote programming according to the present invention and embodiments thereof, wherein a work flow for a remote follow-up use case is exemplarily and schematically illustrated in the form of a block diagram. As an exemplary embodiment, the following describes the present invention from the perspective of the clinical workflow that would be executed by a clinical expert and the patient.

A first step S1 may provide for an authorization by the physician and the patient. For example, prior to any remote follow-up taking place, the responsible physician may authorize the potential remote follow-up for a particular patient. The physician and patient may enter electronic documentation of his/her authorization to allow the remote follow-up via an interface on the clinician programmer 2, patient programmer 3, or other interface. For example, the clinician programmer 2 could include a "terms and conditions" statement for the physician and patient to review and a place to enter a signature via a touch screen interface. This integrated authorization functionality is beneficial to ensure that physician and patient education has occurred and for company liability protection. By collecting the authorization electronically, the clinician programmer 2 could send the authorization information to the central service unit 4. Then the central service unit 4 would in turn check that the authorization is complete before allowing any remote follow-up to take place. Alternatively, the clinician programmer 2 could check with the central service unit 4 that the authorization is complete, and only allow the user to turn on remote follow-up functionality if the authorization is completed.

As a further step S2, in-clinic programming (also referred to as in-office programming) may be carried out. For example, prior to any remote follow-up taking place, the clinical expert may conduct in-office programming using the clinician programmer 2. The clinical expert may set up one or more initial stimulation programs in the therapy device 1 that will be available to the patient on the patient programmer 3. Additionally, the clinical expert may use the clinician programmer 2 to program a setting for remote follow-up to "ON." The option to turn on or off remote follow-up functionality may be one of the settings programmable via the clinician programmer 2 that are specific to the interrogated therapy device 1. Optionally, the clinician programmer 2 could perform a check of central service unit 4 data to ensure that an authorization is on file with the central service unit 4 before it allows the therapy device 1 remote follow-up functionality to be turned on. For example, either before or at the time that the remote follow-up functionality is turned on in the therapy device 1, the clinician programmer may require that the user defines a patient group for the therapy device 1. The clinician programmer 2 user may assign the patient to a defined patient group, which in turn may limit the clinician programmer 2 users who can access the patient via future remote follow-up procedures.

A further step S3 may consist in an initiation of contact: The patient may use the patient programmer 3 as usual during home use. If the patient experiences an issue or question related to the SCS system, the patient and clinical expert may connect verbally and/or visually to discuss the issue. The system 5 may provide a means of verbal and/or visual communication between the clinician programmer 2 and the patient programmer 3, or between a personal phone and either the patient programmer 3 or the clinician programmer 2. Video communication may be included. The interface of the clinician programmer 2 used by the clinical expert may provide a pre-remote checklist or decision-making tool to aid in determining whether the situation described by the patient would be appropriate to try to address with remote follow-up. For example, the interface of the clinician programmer 2 may provide a means for the clinical expert to pull up past data records on in-office or remote follow-ups.

In a further step S4, the clinical expert may go through the pre-remote checklist: If the clinical expert determines that the patient's issue is appropriate to try to address with remote follow-up, the clinical expert may review a checklist of conditions with the patient prior to proceeding with a remote follow-up session. The interface of the clinician programmer 2 used by the clinical expert may provide an electronic checklist or tool to aid in determining whether the patient and SCS system meet all criteria for proceeding with remote follow-up.

Optionally, the interface may require the clinician programmer 2 user to confirm/check off each of the checklist items and/or input information specific to the patient situation/status before it allows the user to proceed with a remote programming session. Optionally, the interface may require a second factor authentication before allowing the remote follow-up to occur. For example, the second factor authentication may be done using biometrics, codes delivered by SMS, Transaction Authentication Numbers, time-based one time factor algorithms, etc.

As a further step S5, a remote interrogation may be carried out: The clinical expert may use the clinician programmer 2 to select the patient device from a list of patient devices that the clinical expert has permission to view (e.g., according to the patient group(s) that the clinical expert has been assigned access). Optionally, the clinician programmer 2 may send a message via the central service unit 4 (which may also be referred to as service center 4) to the patient programmer 3 that the patient must accept before the clinician programmer 2 is allowed remote access to the patient's SCS system. Then, the clinical expert may establish a remote connection to the patient's SCS system via the clinician programmer 2. However, in some embodiments, the acceptance by the patient may not be necessary, since the clinical expert is already authorized to view the patient information remotely, and patient information may be continuously synchronized with the central service unit 4.

For example, in an embodiment, the information may be constantly synchronized on the central service unit 4, i.e., for each change the patient has made in the therapy device 1, the patient programmer 3 immediately synchronizes the status to the central service unit 4. Likewise, the clinician programmer 2 can be synchronized, either immediately in real-time or upon demand by the user (such as clicking a "refresh" button).

In another embodiment, the clinician programmer 2 may be used to send a message via the central service unit 4 to the patient programmer 3, which (if needed) may request a present update from the therapy device 1 and sends this information back to the clinician programmer 2 via the central service unit 4.

In another embodiment, the clinician programmer 2 may be used to send a message directly to the patient programmer 3, which (if needed) may request a present update from the therapy device 1 and sends this information back to the clinician programmer 2.

In any variant, the clinical expert may review information such as, e.g.:
 a. Lead status information (lead impedances and relative lead position)
 b. Whether stimulation is ON or OFF
 c. Presently active program parameters
 d. Other programs and associated parameters that are available to the patient
 e. The present battery status of the therapy device 1
 f Other status information about the therapy device 1 (such as if it is in MRI mode)
 g. Other statistics collected by the therapy device 1 (such as historical stimulation use, activity tracking, posture tracking, etc.)
 g. Other information input by the patient via the patient programmer 3 or otherwise collected by the patient programmer 3 (such as pain survey responses, notes, medication tracking etc.)

In a further step S6, remote adjustments may be performed: The clinical expert may use the clinician programmer 2 to modify parameters of an existing stimulation program or create a new stimulation program. For example, parameter modifications may be displayed locally on the clinician programmer 2 but may not yet be transmitted to the patient's SCS system. For example, the parameters modified on the clinician programmer 2 may include:

a. Frequency or other stimulation timing parameters
    b. Pulse width
    c. Electrode configuration
    d. Balance of amplitudes between subprograms
    e. Program name However, it may be provided that during remote follow-up it is not possible to edit the program amplitude because the amplitude is fixed at minimal dose for any remotely edited program.

A further step S7 may consist in a transmission of update(s): Once all parameter changes are complete for an edited stimulation program, the clinical expert may transmit the edited program. (It should be noted that it may be provided that no changes take place in the patient's therapy device 1 until later steps are completed.) The clinician programmer 2 then may package data about the new stimulation program and send it via the service center 4 to the appropriate patient programmer 3. For example, the transmission of entire programs as a batch rather than incrementally may ensure that parameters are consistent and that network latencies do not result in a partial programming. This may be considered both a safety factor and a usability advantage for both the patient and clinician.

A further step S8 may consist in patient acceptance: After the updates are transmitted by the clinical expert, the patient may receive a message on the patient programmer 3 that the patient is asked to accept the new program. The clinical expert may remain on the phone with the patient to assist with any questions during this process. For example, the patient may click "Accept" to the message. At this time, the program data sent from the clinician programmer 2 may be sent to the therapy device 1. The therapy device 1 may perform a validity check on the newly received program data before loading the new program. In an advantageous variant, the therapy device 1 may check to ensure that the newly received program has an amplitude at minimal dose for safety purposes.

A further step S9 may consist in providing remote programming status to the clinician. For example, as soon as the therapy device 1 is updated, the central service unit 4 may be updated to reflect these new permanent parameters in the therapy device 1. Each time the patient makes subsequent parameter updates (as described below), the therapy device 1 may be updated, and the central service unit's 4 copy of therapy device parameters may be automatically updated.

An amplitude adjustment may be performed in a further step S10: The patient may increase the amplitude of the updated stimulation program as the patient normally would on the patient programmer 3. Optionally, the patient programmer 3 may include prompts to aid the patient with this process. The clinical expert may use the clinician programmer 2 to view the amplitude in near real-time to confirm that the patient is properly adjusting the amplitude. Once the patient reaches a target amplitude, the patient may have the option to use the patient programmer 3 for setting this amplitude as the new default amplitude for the stimulation program.

A further step S11 may relate to reporting: The clinical expert may use the clinician programmer 2 to save the final stimulation program information after the remote follow-up is complete. The clinical expert may be able to store and export a record of the programming to produce a report of the programmed parameters, which can be delivered to or accessed by the following physician. Additionally or alternatively, the record of the programming changes may be automatically saved in the central service unit 4 as well, such that it is available for future query.

Still referring to both FIGS. 1 and 2, the following describes an overview of the sequence of technical steps used to provide a remote follow-up in accordance with one or more embodiments with some additional details on the functions of each component 1-4 of the system 5.

As stated above, the service center 4 (i.e., the central service unit 4) may provide a means of registering clinician programmer 2 users and controlling their access to remote follow-up.

The clinician programmer 2 or other interface may allow the physician and/or patient to electronically provide consent for future participation in remote follow-up. For example, the clinician programmer 2 may have a means of turning on or off the ability to perform future remote follow-ups that can only be accessed during in-person programming. The therapy device 1 then stores this setting. Before a remote follow-up, the clinician programmer 2 may require a user log-in and optionally additional authentication steps before allowing access to remote follow-up. The service center 4 may provide support for user authentication and authorization.

During remote follow-up, the clinician programmer 2 may communicate with the service center 4 in order to display a list of therapy devices 1 that the logged-in user has permission to perform remote follow-ups on, and allow the user to select a therapy device 1 for performing remote follow-up.

The patient programmer 3 may then receive data from the therapy device 1 and update stored data in the service center 4 with the most recent information from the therapy device 1. For example, in some embodiments, the therapy device 1 may package and send data to the patient programmer 3. Alternatively or additionally, the patient programmer 3 may send data directly. For example, the patient programmer 3 may have an option for the patient to manually resynchronize data with the service center 4 or manually turn on and off synchronizing with the service center 4. In a preferred embodiment, the therapy device 1 and patient programmer 3 are continuously synchronized with the service center 4, without any action required by the patient.

The clinician programmer 2 may receive data from the service center 4 (i.e., the central service unit 4) to display the status of the SCS system, such as lead integrity information, battery status, presently used programs, and other statistics available from the therapy device 1.

Further, the clinician programmer 2 provides an interface for the user to edit stimulation parameter settings within an existing program or a newly created program and then transmit the updated parameter settings via the service center 4 and the patient programmer 3 to the therapy device 1. The clinician programmer 2 may have programming rules and calculations that are applied when the user inputs program adjustments. For example, the clinician programmer 2 may place certain restrictions on programming capabilities during the remote follow-up session according to rules that may be configurable. For example, the clinician programmer 2 could limit the range of parameters available to any program that is edited during remote follow-up. Thus, for example, the stimulation amplitude may be fixed at minimal dose for any remotely edited program.

The clinician programmer 2 may reflect (and store) the program parameter changes locally, and then, after the user transmits the updated program, the clinician programmer 2 may send the updated program information to the service center 4. The service center 4 may then send an authentic and valid program update to the therapy device 1 via the patient programmer 3.

For example, the clinician programmer 2 may communicate with the service center 4 over a secure channel using Transport Layer Security (TLS). Access may be authorized, e.g., using a token based system (such as OAuth2) that puts the clinician programmer 2 in regular communication with the service center 4 for the communication of follow-up records and technical communication. For example, this same communication channel may be used to send remote programming commands and ensure that they are transmitted securely to the service center 4.

In an embodiment, the service center 4 may be responsible for mapping patient programmers 3 to the appropriate patient. For example, the service center 4 may maintain a secure communications to each patient programmer 3. All communication may use a TLS channel, for example. Access may be authorized using a token based approach using programmed credentials unique to each patient programmer 3. Again the patient programmer 3 may be in regular communication with the service center 4 to ensure that the service center 4 can collect user data and that any changes the patient makes to their stimulation program is synchronized.

The service center 4 may also maintain a secure channel to the therapy device 1. This may ensure that all messages are sent confidentially, are authentic and are integrity protected even in the event of a compromise of the patient programmer 3.

The patient programmer 3 may receive the transmitted program update from the service center 4 and may provide the patient with a message that the patient is prompted to accept. Once the patient accepts, the patient programmer 3 may send the program update information to the therapy device 1.

The therapy device 1 may load a newly transmitted program. For example, after acceptance by the patient occurs, the remotely sent program may take full effect just as any other permanently stored program in the therapy device 1. In an embodiment, the therapy device 1 checks the authenticity, authorization and/or validity of the received program information. Additionally, the therapy device 1 may ensure that any remotely edited program has an amplitude at minimum dose settings.

The patient programmer 3 may be configured to read and display the updated program information. Further, the patient programmer 3 may be used as usual to adjust the stimulation amplitude or other patient-accessible settings. Importantly, the patient programmer 3 can be used to save a new starting amplitude since remotely edited programs are initially limited to minimal dose amplitude settings.

The patient programmer 3 may synchronize the therapy device 1 programming information back to the service center 4, from where the up-to-date programming information can be read by the clinician programmer 2. For example, the clinician programmer 2 may have a means of refreshing displayed information to reflect the present state of the patient programmer 3 and therapy device 1, so that the user of the clinician programmer 2 can continue to see changes made by the patient during the remote follow-up session.

For example, it should be noted that the method for remote programming a therapy device 1 does not necessarily comprise all steps S1-S11 of the exemplary embodiment described above. Instead, as the skilled person will appreciate, the method may comprise only a subset of said steps in various combinations in some embodiments. Of course, the method may also comprise additional steps.

Further, it should be noted that the method steps S1-S11 described above with reference to FIGS. 1 and 2 may be carried out using the system 5 of FIG. 1. Thus, what has been described above with regard to the method for remote programming a therapy device 1 may analogously apply to the system 5 and its components 1-4 described above, and vice versa.

In the following, further embodiments of the method and system for ensuring patient safety during remote changes to stimulation parameters are described.

During remote programming safety is achieved by ensuring that the therapeutic dose of remote programming is set to a very low level magnitude (the so-called minimal dose amplitude, e.g. zero or close to zero like 0.1 mV) and that the patient is required to increment the magnitude to the appropriate therapeutic level. This allows the patient to discontinue therapy increases if they feel discomfort. This safety feature is guaranteed by the system design such that even in the event of a security vulnerability an attacker cannot bypass this protection mechanism.

It is an objective to come up with a simple way to restrict the impact of cybersecurity vulnerabilities so that they do not have unacceptable risk on patient safety while not making the system overly complex. A particular challenge is that the ultimate asset that needs to be secured is the therapy device has limited compute power and this needs to be factored into the solution. Thus the approach of the system design is to do a defense and depth approach but then to enforce a constraint on the system that the final amplitude of stimulation can only be programmed by the patient and not through remote interfaces.

The system employs a fundamental safety paradigm that ensures new remote programs or changes to any existing program result in the magnitude of the energy being set to zero or effectively zero (e.g. 0.1 mV) and that the system ensures this is done as close to the therapy device as possible. Ideally the therapy device does this as part of accepting incoming commands or creates an interface which does not allow direct programming of amplitudes.

The system 5 comprises a clinician programmer 2, a service center 4, a patient programmer 3 and a therapy device 1 as shown in FIG. 1.

The clinician programmer 2 may be responsible for one or more of the following aspects:

Allowing the user (e.g. a clinician) to enable/disable the remote programming feature (only during an in-clinic follow-up).

Allowing the user to select a patient that they are authorized to remotely program.

Presenting the user interface for the service center 4 to authenticate the user with second factor authentication.

Pulling the therapy device's 1 latest state information from the service center 4 during a remote programming session.

Allowing the user to add/modify a patient's therapeutic program but changed programs are restricted to a non-editable zero amplitude (low dose). This is more of a usability feature than a control at this level.

Definition of the therapeutic program also includes a maximum amplitude limit that is defined by the user.

Only allowing the user to transmit a therapeutic program if the patient programmer 3 has an active connection to the service center 4 and to the therapy device 1.

Relaying the configured therapeutic program to the service center 4 after the user is done making changes.

The service center 4 may be responsible for one or more of the following aspects:

- Authenticating clinician users to log-in to the clinician programmer 2.
- Authenticating clinician users via second factor authentication using the clinician programmer 2.
- Access control to ensure clinicians have access to the appropriate patients.
- Receiving programs from a clinician programmer 2 and routing to the appropriate patient programmer 3.
- Notifying the clinician programmer 2 that it cannot communicate with the patient programmer 3.
- Relaying patient programmer 3 to therapy device 1 connectivity and status is information to the clinician programmer 2.
- Notifying the clinician programmer 2 about the programs' transmission progress.

The patient programmer 3 may be responsible for one or more of the following aspects:

- Receiving programs from the service center 4 over a secure link.
- Prompting the patient as to whether they would like to have remotely transmitted programs to be installed into their therapy device 1.
- Relaying the program to the therapy device 1 if the patient accepts the request.
- Notifying the service center 4 if the patient rejects the request and discarding the request.
- Interrogating the therapy device 1, periodically or on certain events, and forwarding data to the service center 4.
- After receiving successful confirmation from the therapy device 1 that programs were installed, allowing the patient to activate them and configure the amplitude as needed (up to a clinician-specified maximum).

The therapy device 1 may be responsible for one or more of the following aspects:

- Receiving programs from the service center 4 over a secure link.
- Ensuring the program(s) was/were sent from a valid sender using cryptographic controls.
- Ensuring that the starting amplitude for the initial program is set to the minimal dose amplitude (see below).
- Installing the received programs if valid.
- Rejecting them if invalid.
- Sending a confirmation to the patient programmer 3 that it has accepted or rejected the remote program(s).

The therapy device is a complex device with a large number of programs with each program containing a set of N sub-programs (N being a natural number) resulting in a large number of potential inconsistencies and errors that could cause the device to behave incorrectly. To protect against this, an option could be to architect a system with parameter rules processing in the therapy device but this would result in a significant amount of processing complexity over traditional solutions in this space. Also, some parameter settings may make logical sense and pass standard checks but still result in harm when targeted to a specific patient making this solution impossible in practice. For example, amplitude ranges that are required to give adequate therapy in some patients can cause pain in others. Thus, there is not a general set of parameter ranges that make sense or are effectively safe for all patients.

The amount of energy delivered to the patient may be a function of the frequency, pulse width, electrode configuration and/or pulse amplitude. The present approach limits the starting amplitude for all therapies to a minimal dose amplitude (zero or a very low value like 0.1 mV) and requires the patient to then increment the amplitude to a desired level communicated to them from the clinician. As the patient is in control of incrementing the amplitude he/she can control the dose in discrete increments and stop if discomfort is felt. There is clinical data to support that (1) patients will feel sensation from stimulation prior to discomfort, and (2) patients will perceive discomfort prior to any damaging effect from stimulation. Therefore, the approach of starting the amplitude at the minimal dose amplitude and relying on the patient to increase it ensures safety even in the event of a malicious programming. A malicious programming attempt could be targeted at multiple attack surfaces in the system. For instance, a hacker with sufficient technical knowledge could bypass controls on the programming interface (web or application) to send a malicious set of parameters to the therapy device or could manipulate programming commands in transit to the therapy device. Having a simple mechanism in the therapy device as described herein, protects from multiple different avenues of attack.

In order to ensure a program is valid, including having a zero (or very low) starting amplitude, a program that is sent remotely will arrive to the patient programmer in a manner that allows the therapy device to identify the program has been sent through the remote programming channel. When the therapy device receives a new or updated program via the remote programming channel, the therapy device may decrypt and/or integrity check the contents of the program using cryptographic functions that are unique to the remote channel. One way to accomplish this may be to ensure all communication to a therapy device is routed through a secure service center. The service center may have factory shared credentials unique to each therapy device that may be used with encryption and/or authentication algorithms to protect each message. The therapy device may check the program contents against a set of rules, at least including the zero amplitude rule, to ensure that the program contents received are appropriate to those allowed via the remote channel. If the program contents do not pass the check, the therapy device will actively reject the program (meaning it will not be allowed to be written to working memory of the therapy device). If the program contents received pass the check, the therapy device may write the program to its working memory.

Optionally, the patient programmer itself may additionally check the contents of the program against a set of rules to determine if the program is valid, including having a starting amplitude with a minimal dose amplitude.

Figure 3:
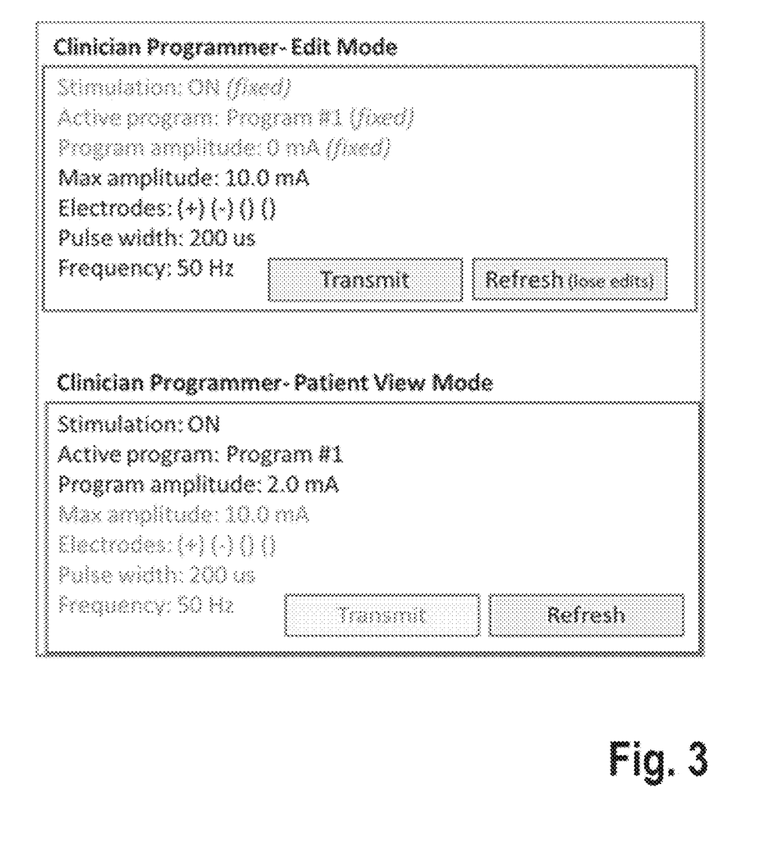
FIG. 3 schematically and exemplarily illustrates shows an embodiment of an interface of the clinician programmer in edit mode (upper part) and in patient view mode (lower part)
Figure 4:
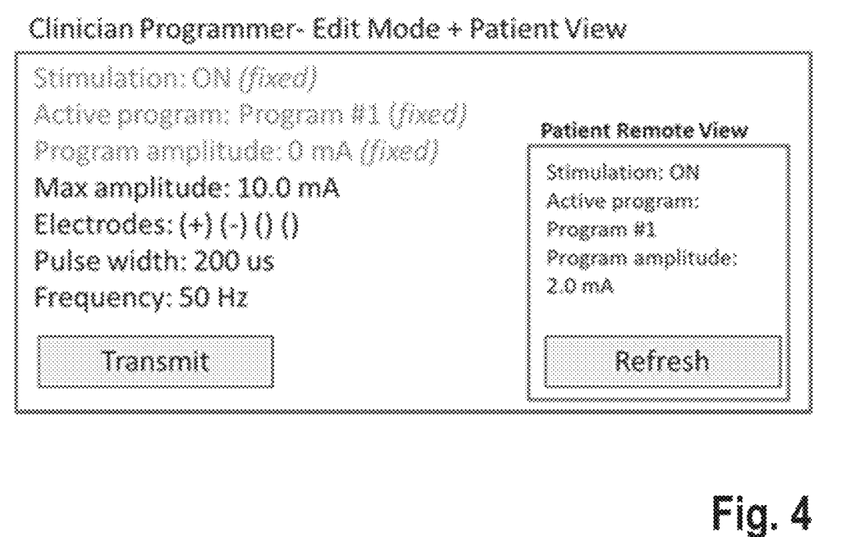
FIG. 4 schematically and exemplarily illustrates shows another embodiment of the interface of the clinician programmer with a combined edit mode and patient view mode.

In one embodiment, a patient may have a therapeutic program consisting of a single sub-program. In this case, the clinician programmer needs to send a single zero (or low) amplitude down to the therapy device and then the patient can use the patient programmer to ramp the amplitude to the desired level. In this case, the zero amplitude rule would be verifying that the stimulation amplitude equals zero. Optionally, the user of the clinician programmer can set a maximum amplitude for the program that the patient will not be allowed to exceed. Meanwhile, the clinician programmer provides the ability for the user to view the present active parameters as controlled by the patient on the patient programmer. This could be done in the form of a "refresh" button to toggle between editing mode and patient-view mode. Or, the clinician programmer could have a built-in real-time display of the patient parameters (which could include a view of the patient programmer screen itself). These options are shown in FIG. 3 and FIG. 4.

Figure 5:
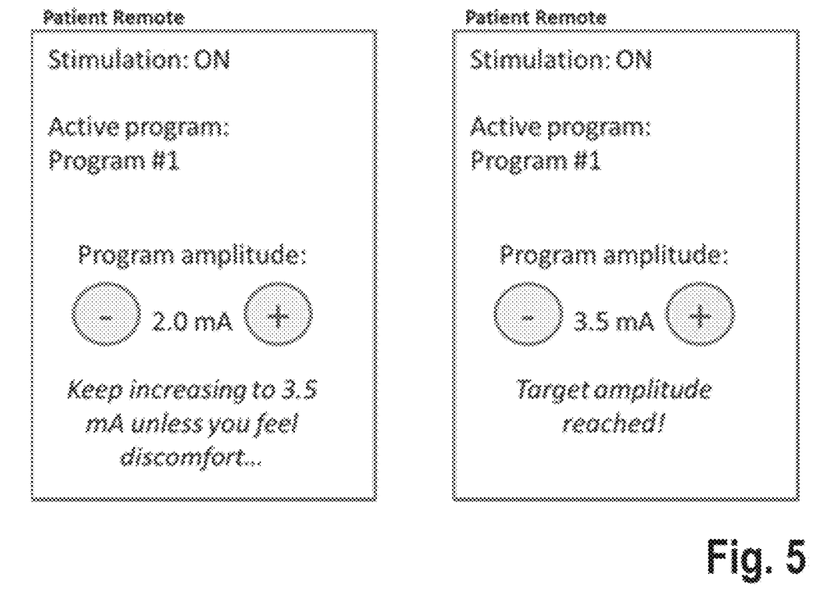
FIG. 5 schematically and exemplarily illustrates shows an embodiment of an interface of the patient programmer for adapting the amplitude.

Alternatively, the design could send a final target amplitude which the therapy device uses for informational purposes (such as being displayed on the patient programmer as an indicator of the desired target amplitude) and the therapy device starts the stimulation at the minimal dose amplitude. Again, commands from the patient programmer are used to ramp the stimulation to the desired safe and comfortable level. An example of the user interface on the patient programmer in the case that of target amplitude is shown in FIG. 5.

In another embodiment, a therapeutic program may comprise multiple sub-programs. In this case, a vector of amplitudes (comprising one amplitude for each sub-program) needs to be transmitted to the therapy device and the solution for ramping the amplitudes to the target amplitudes must take into account that all amplitudes have to be zero (or low) initially but that the clinician needs to be able to set the relative amplitudes between the sub-programs to control patient comfort and therapy success. For instance at the target stimulation level, a first sub-program on a first set of electrodes (e.g. electrodes A and B) may need to be at 3 mA whereas a second sub-program on a second set of electrodes (e.g. electrodes B and C) may need to be 2 mA. Thus the system design needs to:

start the amplitude values at zero,
have the amplitudes ramp up to the desired values in an incremental fashion such that the patient can feel an increase in stimulation over a number of steps, and
ensure the relative difference in the target amplitudes is as the clinician desires.

Various approaches can achieve this, such as (but not limited to):

(1) Sending the final target amplitudes from the clinician programmer and having the therapy device calculate starting amplitudes to use for stimulation that start at zero and increment in a monotonic manner so that all amplitudes reach their respective target values at the same time. The ramp can be linear or in a ratio fashion. An example would be determining the stimulation delivered as a ratio of strength times the final value. Strength starts at zero and is not programmable. Here no explicit zero amplitude rule is needed as the remote user does not have the ability to program the starting amplitude.

Figure 6:
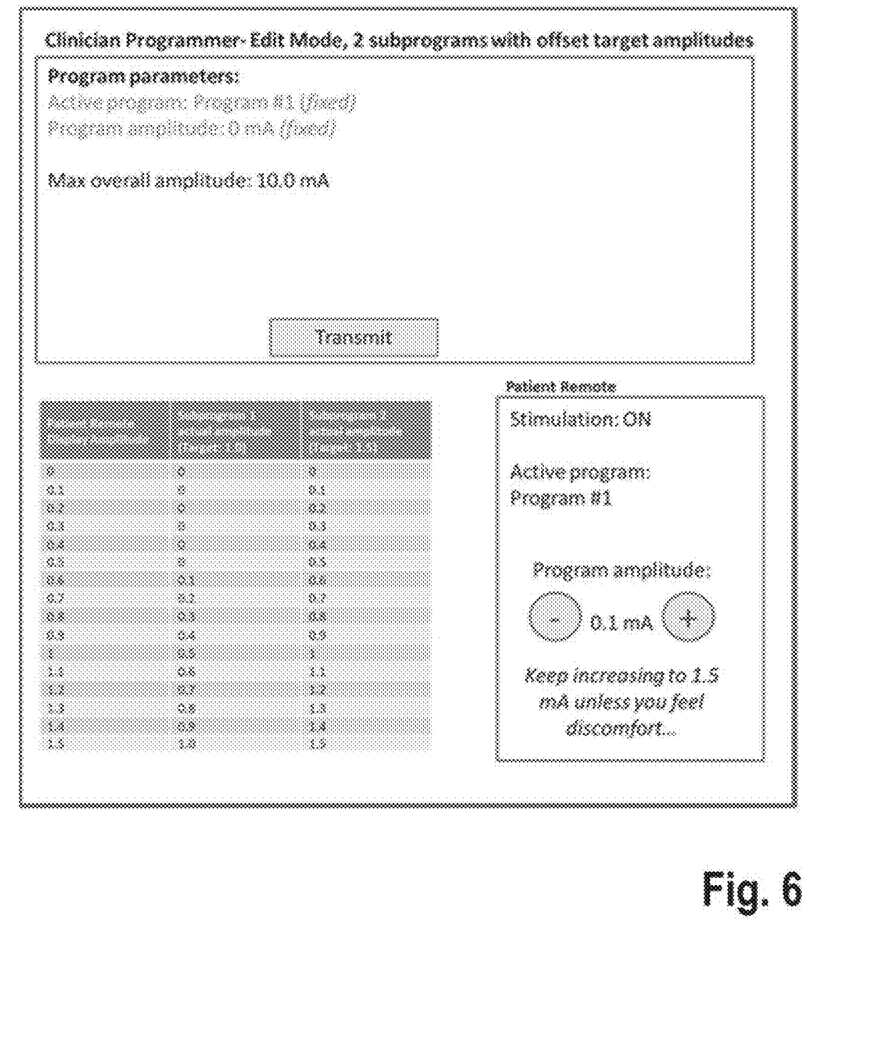
FIG. 6 schematically and exemplarily illustrates shows an embodiment of an interface of the clinician programmer in edit mode with two sub-programs (upper part) and an embodiment of an interface of the patient programmer for adapting the amplitude (lower right part).

(2) Sending values less than zero, where the highest amplitude is set to zero and the others are negative offsets. The design then ensures that negative values result in no stimulation being delivered. The amplitudes of the sub-programs are then incremented in a linear fashion. As they become positive they become active and therapy is delivered. An illustration of this behavior is shown in FIG. 6. In the case shown, the user of the clinician programmer defines the target subprogram amplitudes, and the clinician programmer converts these to offset values. These offset values are used to determine each subprogram amplitude relative to the amplitude displayed on the screen. Here the zero amplitude programming rule would enforce all starting amplitudes are less than or equal to zero.

Also, the therapy device may maintain multiple connections with one or more external device(s) and each one may have a different level of access or trust such that the therapy device can allow some selected commands on some interfaces and not on others. In the example system shown in FIG. 2, the therapy device has three external connection types:

A clinician programmer connection which is duration limited but allows access to all commands.
A patient programmer connection which is a long-term connection but only allows access to limited set of commands. Example limitations would be that it cannot change the maximum stimulation amplitude but can increment the amplitude up to this point.
A remote programming connection which is long term which allows new programs to occur but ensures that they have zero amplitude. This connection also does not allow usage of any commands to increment amplitude of the device.

In the case of clinician programmer or patient programmer connection, such connections may be established dynamically. This means using a pairing process which may combine physical proximity along with a combination of cryptographic measures to ensure security. Many solutions are possible, for example application of a magnet for ensuring proximity and then mutual cryptographic authentication and key agreement using certificates and algorithms such as Diffie-Hellman. The result is the sharing of one or more symmetric keys that are unique and specific to the type of connection.

In the case of the remote programming connection it is possible to pre-share one or more symmetric keys to establish a secure channel at the factory between a service center and a therapy device. It would also be possible to pre-share certificates and have the service center and the therapy device perform mutual authentication and key agreements to derive symmetric keys on an as needed basis. Again, this key is specific to the remote programming connection and all remote programming must be pass an cryptographic integrity check to prove they came over the correct channel and that they have not be tampered with.

Thus each connection may be subject to an authentication technique prior to making the connection and then thereafter all communication is protected by security controls and credentials unique to each connection.

A combination of these access rules and the zero amplitude approach may result in a defense in depth architecture where an attacker would need to compromise multiple sub-systems in order to result in harm to the patient via the remote programming interface. For instance, they would need to first send a program to the therapy device using a remote programming connection that passes all cryptographic controls. At this the system would be in unexpected state but still no harm to the patient has occurred. They would then need to compromise the specific patient programmer associated with that patient to send commands to increment the amplitude.

In one embodiment, a system for safely starting a therapy program is provided. The system may comprise:

a clinician programmer (or a web-based user interface) which is configured to create a program (e.g. by creating a new program from scratch or by modifying an existing program);
a therapy device (e.g. an implantable medical device like a neurostimulator) comprising a processor, wherein the processor is configured to execute the program;
a service center (e.g. a remote server);
a patient programmer (or relay device); and
a communication network that is configured to communicate the program from the clinician programmer to the therapy device, e.g. via the service center and/or via the patient programmer.

The patient programmer may be configured to
be operated by the patient;
receive at least program installation instructions from the service center; and/or transmit the program installation instructions to the therapy device,
wherein the program installation instructions, when executed by the processor, comprise is instructions to install the program on the therapy device.

The processor of the therapy device may be configured to
maintain one or more separate secure communication channels depending on external actors wishing to communicate with the therapy device (e.g. clinician programmer via a local session, patient programmer, remote programming via the communication network);
receive a program from the communication network via a communication channel (e.g. a remote programming connection);
decrypt and integrity check the contents of the program;
evaluate that the commands received of the program are appropriate to those allowed via a remote channel and actively reject commands that are not appropriate; and/or
execute the program (or multiple programs) with a minimal dose amplitude (e.g. zero amplitude or a similar effectively low therapeutic dose like 0.1 mV).

It may only be possible to increment the amplitude of the program over the patient programmer interface. This allows the patient to increment the parameters in a manner such that the patient can react on feeling discomfort and that the relative amplitudes of the sub-programs at the target values are as the clinician desired.

The clinician programmer (or web-based user interface) may have the ability for the user to:
define a maximum amplitude for a program;
define offsets between sub-program amplitudes;
define amplitudes for the program or subprograms; and/or
view (e.g. in real time) the present parameters that are active in the therapy device and controlled by the patient programmer.

The patient programmer may have the ability to
check the suitability of a remotely received program;
guide the user to increment the amplitude to a target amplitude; and/or
maintain offsets between subprogram amplitudes.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Therapy device
2 Clinician programmer
3 Patient programmer
4 Central service unit
5 System
S1-S11 Method steps

The invention claimed is:

1. A method for remote programming a therapy device for neurostimulation, comprising:
generating a stimulation program for the therapy device by means of a clinician programmer;
transferring the stimulation program to a patient programmer;
loading the stimulation program on the therapy device from the patient programmer;
increasing a stimulation amplitude of the stimulation program by means of the patient programmer;
wherein an initial stimulation amplitude setting of the stimulation program is limited to a minimal dose amplitude by means of the patient programmer, wherein the minimal dose amplitude may be such that safety of the patient is guaranteed.

2. The method of claim 1, wherein the therapy device performs a validity check on the newly received stimulation program before loading the stimulation program.

3. The method of claim 2, wherein the validity check comprises checking if the stimulation program has an amplitude at minimal dose.

4. The method of claim 1, wherein the clinician programmer is used to view the stimulation amplitude in near real-time.

5. The method of claim 1, wherein the method further comprises accepting the transferred stimulation program by means of the patient programmer before it is loaded on the therapy device.

6. The method of claim 1, wherein the stimulation program is transferred from the clinician programmer to the patient programmer via a central service unit.

7. The method of claim 1, wherein before generating the stimulation program the clinician programmer receives status information of the therapy device.

8. The method of claim 1, wherein increasing the stimulation amplitude of the stimulation program from the minimal dose amplitude by means of the patient programmer is performed manually.

9. The method of claim 1, wherein increasing the stimulation amplitude of the stimulation program from the minimal dose amplitude by means of the patient programmer is performed in incremental steps.

10. A system for remote programming a therapy device for neurostimulation, the system comprising:
a therapy device being configured for providing electrical stimulation pulses for neurostimulation;
a clinician programmer being configured for generating a stimulation program for the therapy device;
a patient programmer being configured for receiving the stimulation program, the therapy device being configured for loading the stimulation program from the patient programmer,
wherein a stimulation amplitude setting of the generated stimulation program is limited to a minimal dose amplitude by means of the patient programmer, wherein the minimal dose amplitude may be such that safety of the patient is guaranteed.

11. The system of claim 10, further comprising a central service unit being configured for facilitating communication between the clinician programmer and the patient programmer.

12. The system of claim 11, wherein the central service unit is configured for serving as a central data repository.

13. The system of claim 10, wherein the therapy device is configured for performing a validity check on the newly received stimulation program before loading the stimulation program.

14. The system of claim 13, wherein the validity check comprises checking if the stimulation program has an amplitude at a minimal dose.

15. The system of claim 10, wherein the patient programmer allows for adjusting the stimulation amplitude.

16. The system of claim 15, wherein the patient programmer and/or the therapy device allows for setting a new stimulation amplitude as a new default amplitude of the stimulation program.

17. The system of claim 15, wherein the clinician programmer allows for viewing the stimulation amplitude in near real-time.

18. The system of claim 10, wherein the patient programmer provides for manual increasing of the stimulation amplitude from the minimal dose amplitude.

19. The system of claim 10, wherein the patient programmer provides for increasing of the stimulation amplitude from the minimal dose amplitude in an incremental fashion.

* * * * *